(12) United States Patent
Pison et al.

(10) Patent No.: US 9,366,623 B2
(45) Date of Patent: Jun. 14, 2016

(54) OPTICAL ANALYSIS METHOD FOR LIQUID IN A SAMPLE CONTAINER AND ANALYSIS DEVICE FOR CARRYING OUT THE METHOD

(75) Inventors: Daniela Pison, Chur (CH); Friedrich Neuhaeusser-Wespy, Zurich (CH); Stefan Gluekler, Chur (CH); Johann Seeber, Chur (CH); Urs Gredig, Andeer (CH); Michael Spoerri, Bonaduz (CH)

(73) Assignee: Hamilton Bonaduz AG, Bonaduz (CH)

( * ) Notice: Subject to any disclaimer, the term of this patent is extended or adjusted under 35 U.S.C. 154(b) by 408 days.

(21) Appl. No.: 13/980,101

(22) PCT Filed: Jan. 25, 2012

(86) PCT No.: PCT/EP2012/051087
§ 371 (c)(1),
(2), (4) Date: Jul. 17, 2013

(87) PCT Pub. No.: WO2012/101146
PCT Pub. Date: Aug. 2, 2012

(65) Prior Publication Data
US 2013/0293706 A1    Nov. 7, 2013

(30) Foreign Application Priority Data
Jan. 25, 2011  (DE) .......................... 10 2011 003 140

(51) Int. Cl.
*G01N 21/51*  (2006.01)
*G01N 13/00*  (2006.01)
(Continued)

(52) U.S. Cl.
CPC ................ *G01N 21/51* (2013.01); *G01N 13/00* (2013.01); *G01N 35/00732* (2013.01); *G01N 15/1463* (2013.01); *G01N 2035/00801* (2013.01)

(58) Field of Classification Search
CPC ...... A61B 1/05; A61B 1/0607; A61B 1/0638; A61B 1/0684; A61B 2562/0242; A61B 5/0048; A61B 5/0059; A61B 5/0071; A61B 5/0075; A61B 5/411; A61B 5/415; A61B 5/418; A61B 5/444; A61B 5/445; A61B 5/72
See application file for complete search history.

(56) References Cited

U.S. PATENT DOCUMENTS 4,480,910 A * 11/1984 Takanashi ............. G03F 7/2041
355/30
5,510,620 A    4/1996 Achter et al.
(Continued)

FOREIGN PATENT DOCUMENTS

DE        19742160 A1    4/1998
DE     112004000698 T5    3/2006
(Continued)

OTHER PUBLICATIONS

Search Report for German Application 10 2011 003 140.5 dated Jun. 6, 2011, 5 pgs.
(Continued)

*Primary Examiner* — Sath V Perungavoor
*Assistant Examiner* — Peter D Le
(74) *Attorney, Agent, or Firm* — Rothwell, Figg, Ernst & Manbeck, P.C.

(57) ABSTRACT

The invention relates to a method for optically analyzing a sample liquid (34) contained in a sample container (24*a-h*), wherein the sample liquid (34) contains at least one substance (40) in at least partially dissolved form, comprising the following steps: providing at least one sample container (24*a-h*) filled with sample liquid (34); illuminating the at least one sample container (24*a-h*) by means of a light source (18*a-h*); and recording an image of an identification pattern (32*a-h*) associated with the at least one sample container (24*a-h*) by means of an image recording device (22) that produces image data, wherein the optical path (OP) is selected in such a way that the sample liquid (34) contained in the at least one sample container (24*a-h*) lies at least partially between the image recording plane (36) of the image recording device (22) and the identification pattern (32*a-h*). The invention further relates to an analysis device for carrying out the method.

16 Claims, 4 Drawing Sheets

(51) Int. Cl.
*G01N 35/00* (2006.01)
*G01N 15/14* (2006.01)

(56) References Cited

U.S. PATENT DOCUMENTS

| | | | | |
|---|---|---|---|---|
| 5,581,071 A | * | 12/1996 | Chen | G06K 7/10851 235/455 |
| 6,122,042 A | | 9/2000 | Wunderman et al. | |
| 6,782,122 B1 | * | 8/2004 | Kline | G01F 23/292 250/223 B |
| 8,708,548 B2 | * | 4/2014 | Engelhardt | G01N 13/00 356/427 |
| 2005/0219523 A1 | * | 10/2005 | Onuma | G01N 21/9027 356/239.5 |
| 2010/0027868 A1 | * | 2/2010 | Kosaka | G01N 33/4905 382/134 |
| 2010/0201792 A1 | * | 8/2010 | Brinz | G01N 21/4738 348/61 |
| 2010/0252635 A1 | * | 10/2010 | Drzymala | G06K 7/10722 235/462.41 |
| 2011/0066382 A1 | * | 3/2011 | Adams | G01N 15/147 702/19 |
| 2011/0102542 A1 | * | 5/2011 | Chen | G06T 3/4038 348/37 |
| 2011/0106312 A1 | * | 5/2011 | Chen | B25J 9/1697 700/259 |

FOREIGN PATENT DOCUMENTS

| | | |
|---|---|---|
| DE | 102004056698 B3 | 8/2006 |
| DE | 202004021397 U1 | 11/2007 |
| DE | 102007063428 A1 | 5/2009 |
| DE | 102007062250 A1 | 6/2009 |
| DE | 102008026803 A1 | 12/2009 |
| EP | 2120038 A2 | 11/2009 |

OTHER PUBLICATIONS

Office Action issued in European Application 12 708 722.9, dated Nov. 16, 2015, 6 pgs.

* cited by examiner

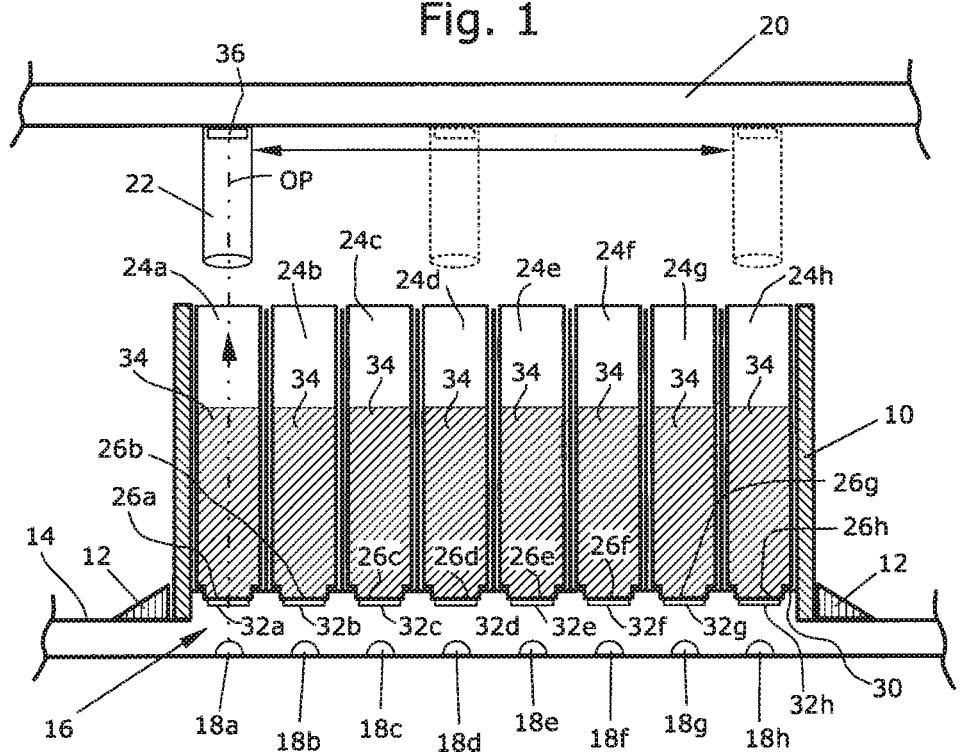
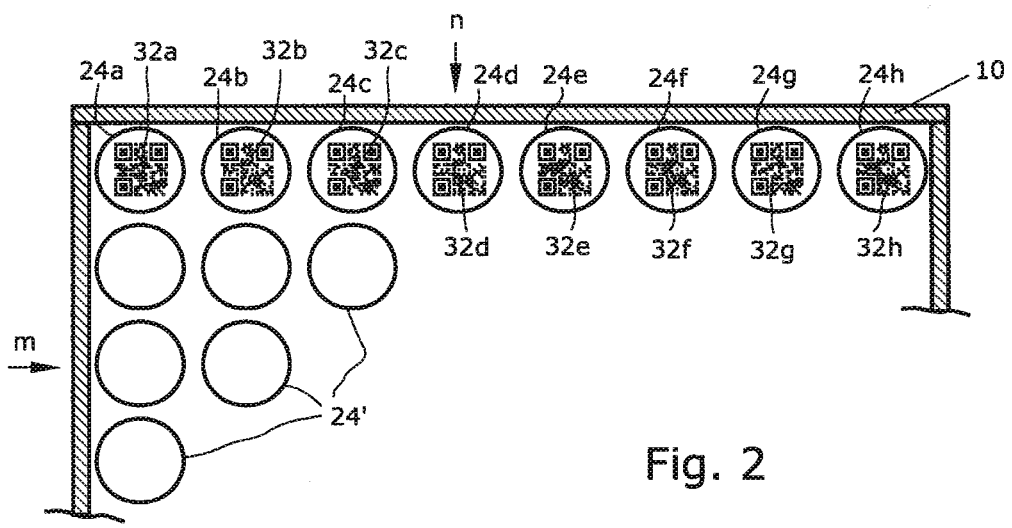

OPTICAL ANALYSIS METHOD FOR LIQUID IN A SAMPLE CONTAINER AND ANALYSIS DEVICE FOR CARRYING OUT THE METHOD

CROSS REFERENCE TO RELATED APPLICATION

This application is a 35 U.S.C. 371 National Phase Entry Application from PCT/EP2012/051087, filed Jan. 25, 2012, which claims the benefit of German Patent Application No. 10 2011 003 140.5 filed on Jan. 25, 2011, the disclosure of which is incorporated herein in its entirety by reference.

The present invention relates to a method for the optical analysis of a sample liquid contained in a sample container, wherein the sample liquid contains at least one substance in at least partly dissolved form. The invention furthermore relates to an analysis device configured to carry out the method.

Known optical analysis methods, such as stray-light measurements or absorption measurements can be used to capture undissolved or not completely dissolved particles of a substance, which are present in a sample liquid. Complete dissolution of the substance in a liquid can be monitored on the basis of such measurements. However, such analysis methods are quite complicated, particularly in respect of the detection devices for measuring stray light or absorption required for this.

In the automated analysis of sample liquids, for example when using a metering apparatus, in particular an automated pipetter, it is often the point to be able to verify or monitor with sufficient reliability the complete dissolution of a previously solid substance in the sample liquid. However, should the substance only be partly dissolved, it is generally not important in such automated analyses to be able to determine precisely the degree of the dissolution of the substance, as is possible in the case of known stray-light or absorption methods.

It is an object of the invention to provide an optical analysis method and an associated analysis device, which enables a simplified determination of the degree of dissolution, in particular of the complete dissolution of a substance in a sample liquid.

In order to achieve this object, it is proposed that the method comprises the following steps:
providing at least one sample container filled with a sample liquid; illuminating the at least one sample container by means of a light source; and capturing an image of an identification pattern associated with the at least one sample container by means of an image recording device which generates image data, wherein the optical path is selected in such a way that the sample liquid contained in the at least one sample container is at least partly situated between the image recording plane of the image recording device and the identification pattern.

By selecting the optical path between image capture plane and the identification pattern in such a way that the sample liquid, in particular a sub-volume or the whole volume of the sample liquid, lies in the optical path, the image of the identification pattern is recorded through the sample liquid. However, the image data of which it is expected that they represent the identification pattern may possibly also contain particles still contained in the sample liquid, and so there may be regions in the image of the identification pattern which cannot be identified unambiguously. Hence, by recording an image of the identification pattern, it is possible to establish in a simple manner whether or not the substance to be dissolved in the sample liquid has been completely dissolved.

The image capture plane is preferably formed by an image sensor such as a CCD sensor or CMOS sensor, which is housed in a suitable manner in an associated analysis device, for example in a camera.

A light source is preferably associated with the at least one sample container. The desired illumination conditions for capturing the image data of the identification pattern can be established by means of such a light source.

In this respect, it is furthermore proposed that the light source or each light source is set in terms of its brightness. The brightness can be selected depending on, for example, the color of the sample liquid such that the identification pattern can be captured due to sufficient illumination in a relatively dark but nevertheless transparent sample liquid.

After the image of the identification pattern has been recorded, the generated image data can be evaluated and it can be established whether the identification pattern can be identified through the sample liquid with the generally dissolved substance contained therein. If the identification pattern is identified as such, this can lead to the conclusion that the substance has dissolved to a very high degree or completely dissolved since the identification of the identification pattern has not been adversely affected by undissolved substance particles in the sample liquid.

Preferably, after identifying the identification pattern, it is established whether the identification pattern has been identified with or without error correction. Identifying the identification pattern using the error correction in the identification algorithm can provide an indication that, although the identification pattern could be identified, there are relatively small errors in the recorded image of the identification pattern. By way of example, this can be traced back to small substance particles which are still contained in the sample liquid in an undissolved form.

It is proposed that, if the identification pattern of the at least one sample container is not identified, the presence of an undissolved substance in the sample liquid is assumed as a result; in particular, the sample liquid is assumed to be turbid. Hence, if the identification pattern is not identified, the assumption can generally always be made that this is a non-transparent (not completely transparent) sample liquid.

If the identification pattern of the at least one sample container is identified, it is preferably established how large the error correction is and it is possible to derive therefrom whether the substance is partly or completely dissolved in the sample liquid. The basic identification of the identification pattern can also occur if small substance particles and/or a small amount of substance particles are still present in the sample liquid in an undissolved state. As a result of the size of the error correction, it is possible to estimate how high the degree of dissolution of the substance is, without actually having to determine it quantitatively. It is possible to determine error correction values which indicate a sufficient dissolution of the substance and the substance liquid of the relevant sample container can be cleared for further processing as a result thereof.

The brightness of the light source can be set depending on the identification of the identification pattern.

Alternatively, or in addition thereto, the exposure duration of the image recording device can be set depending on the identification of the identification pattern.

The aforementioned method steps can also at least in part be carried out several times for the at least one sample container, wherein, preferably, in the case of each renewed run-through, the brightness of the light source and/or the exposure duration of the image recording device is modified.

Repeatedly carrying out steps for identifying the identification pattern renders it possible to exclude misinterpretations of not identified identification patterns in the case of a first or only run-through of an identification, in particular of an identification algorithm.

The invention also relates to an analysis device for carrying out one or more of the above-described method steps, wherein the analysis device comprises:

at least one light source for illuminating at least one sample container held in a holding container, wherein the holding container and the light source can preferably be moved relative to one another and wherein an identification pattern is arranged on the sample container, at least one image recording device for capturing the identification pattern of the at least one sample container, wherein the image recording device and the holding container are arranged in such a way that they can move relative to one another, wherein, in relation to the optical path, the image recording device is provided on the analysis device in such a way that the sample liquid contained in the at least one sample container is at least partly situated between the image recording plane of the image recording device and the identification pattern.

Light originating from the light source is preferably guided in such a way that it irradiates the at least one sample container on the underside thereof.

In this respect, it is proposed that the light source is arranged below the holding container or the at least one sample container situated therein.

The image recording device is preferably arranged above the sample container irradiated by the light source. Camera-like instruments, which, for example, can be moved to the individual sample containers in order to capture the associated identification pattern, can be used as image recording device.

The holding container is preferably configured in such a way that a plurality of sample containers can be held therein in the style of a matrix with n columns and m rows. A particularly preferred embodiment of the holding container comprises 8 rows and 12 columns such that 96 sample containers can be held therein. However, in so doing, it is not necessary for carrying out the method above that all individual holding spaces of the holding container are equipped with a sample container; i.e. the holding container can be partly filled or completely filled with sample containers.

In this context, reference is also made to the fact that the image recording device may comprise a plurality of cameras arranged next to one another, which are able to record simultaneously sample containers, or the identification patterns thereof, which lie next to one another.

It is proposed that the light source is formed by a plurality of light-emitting diodes, which are preferably arranged in a manner corresponding to the matrix arrangement of the holding container, in such a way that a light-emitting diode can be associated with each sample container of the holding container. It is also feasible for a plurality of light-emitting diodes to be associated with each sample container in order, when necessary, to be able to generate more light for the relevant sample container; for example, the light-emitting diodes could be arranged in pairs or in groups of three, respectively, in accordance with the matrix of the holding container.

The identification pattern on the at least one sample container is preferably provided on the underside thereof, wherein the identification pattern is preferably formed by various regions with different light transmission properties.

By way of example, a barcode in the form of a product code or a two-dimensional 2D barcode can be used as identification pattern.

It is proposed that the analysis device furthermore comprises a control device or has a communication link thereto, which control device is configured in such a way that the actuation of the relative movements between holding container, light source and image recording device can be carried out and that the method steps required for the optical analysis of the sample liquid can be carried out.

The above-described analysis device is preferably part of a metering apparatus, in particular an automated pipetter. Here, the control device mentioned above with reference to the analysis device can, at the same time, also be the control device of the metering apparatus, particularly within the meaning of a computer unit, which actuates the metering device, is known per se and comprises a processor, memory, etc. and communication links for transmitting commands/signals to components of the metering apparatus or the analysis device.

The presented method is preferably carried out by means of a computer program which is stored in a memory of the control device and can be executed by a processor of the control device.

The invention will be explained below in an exemplary and non-restrictive fashion with reference to the attached figures.

FIG. 1 shows a simplified schematic partial sectional view of a holding container with sample containers in an analysis device for capturing identification patterns.

FIG. 2 shows a top view of part of the holding container from FIG. 1 with visible identification patterns.

Figure 3:
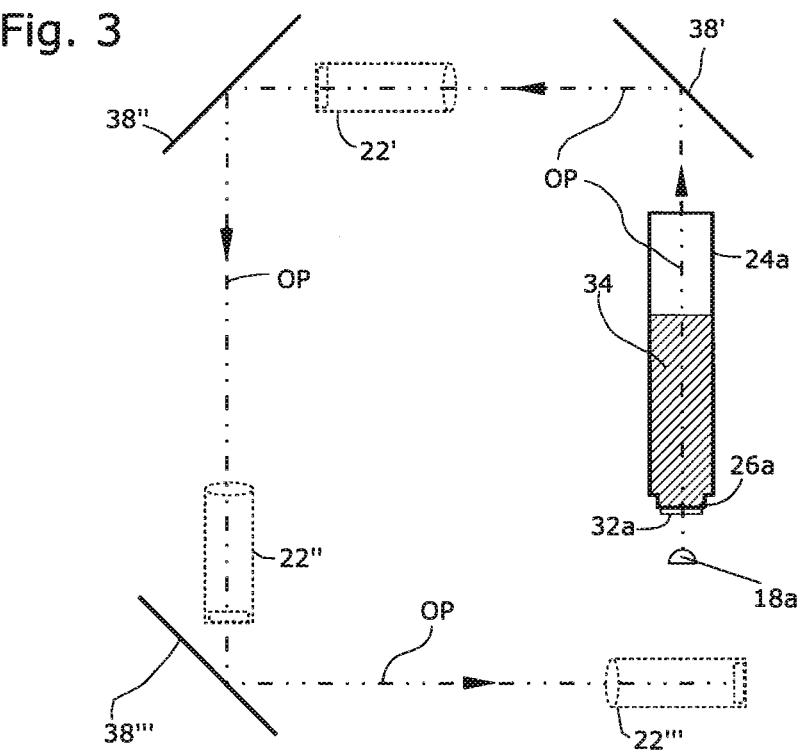
FIG. 3 shows possible optical arrangements for a recording device in a simplified and schematic fashion.

FIG. 1 shows, in a simplified and schematic fashion, a holding container 10, which is situated in a metering apparatus (only illustrated in part) such as an automated pipetter. The holding container is arranged at a position on the metering apparatus by means of guide elements 12, at which position a base plate 14 of the metering apparatus has an opening 16. A light source in the form of a plurality of light-emitting diodes 18a-h is arranged under this opening 16. It is possible to see a support 20 above the holding container 10, on which support an image recording device 22, such as a digital camera, is attached in a preferably movable fashion; this is indicated by the double-headed arrow and camera positions illustrated in a dashed manner. It is also feasible that the support overall is a movable component of the analysis device or the metering apparatus.

A plurality of sample containers 24a-h are held in the holding container 10, the former standing with their lower ends 26a-h having a slightly smaller diameter in corresponding openings in the base 30 of the holding container 10. An identification pattern associated with the respective sample container is denoted by 32a-h on the underside of each sample container. Each sample container 24a-h is filled with a sample liquid 34.

In order to establish by means of an optical analysis whether a substance to be dissolved in the sample liquid has been completely dissolved, the sample containers 24a-h are illuminated from below by the respective light-emitting diode 18a-h such that the camera 22 arranged over a relevant sample container 24a-h is able to record an image of the respective identification pattern 32a-h. To this end, the identification pattern 32a-h has regions which transmit light and are opaque to light, as can be identified in an exemplary fashion in the top view in accordance with FIG. 2 for the sample containers 24a-h and the associated identification patterns 32a-h, which are embodied here in an exemplary fashion as 2D barcode but can also be any other suitable type of code, such as 1D barcodes, additional digits or the like.

With reference to FIG. 2, reference is also made to the fact that the sample containers 24a-h, 24' are preferably arranged in a matrix in the holding container 10. A preferred size are holding containers with 96 sample containers, arranged in 8 columns (n) and 12 rows (m). Naturally, any other size of holding container may be employed. It is also feasible for the arrangement of the sample containers not to be in the shape of the matrix, but rather, for example, they could be arranged along a circumference in the case of a round holding container, wherein further sample containers could also be arranged within this circumference.

As can be seen from FIG. 1, the optical path OP (dash-dotted arrow line) extends between the light source, in this case light-emitting diode 18a, and the camera 22 or an image sensor (CCD, CMOS or the like) 36 representing the image plane. Here, the sample liquid to be examined is situated between the identification pattern 32a and the image plane 36 such that the identification pattern 32a, as seen from the camera 22, must be identified through the sample liquid 34. In the present case, the optical path OP traverses the entire height of the volume of the sample liquid 34 contained in the sample container 24a. In other words, the camera 22 looks onto the identification pattern 32a through the entire volume of the sample liquid 34.

In another configuration, it would also be feasible for the camera not to be aligned from the top, but rather, for example, be aligned from the side onto the sample container and only peering through a partial volume of sample liquid, i.e. only in part through the sample liquid, to a corresponding identification pattern applied at a different location on the sample container (side wall). A reversal of the situation illustrated in FIG. 1, for example in such a way that a type of cover with identification pattern is applied onto each sample container and then recorded through the sample liquid by a camera situated under the sample container, is also feasible. In such a case, illumination would take place from above onto the cover of the sample container.

Further alternatives of the optical path OP are indicated in FIG. 3. It is by all means feasible for the camera 22', 22", 22'" to be arranged at different positions of the metering apparatus, wherein the optical path OP is guided to the respective camera 22', 22", 22'" by respective deflection means 38', 38", 38'", particularly mirrors. The options illustrated here for guiding the optical path are purely exemplary. Depending on the embodiment of the associated metering apparatus, the optical path can also be guided in other directions, around other angles or with the use of further optical components, such as lenses and the like.

Figure 4:
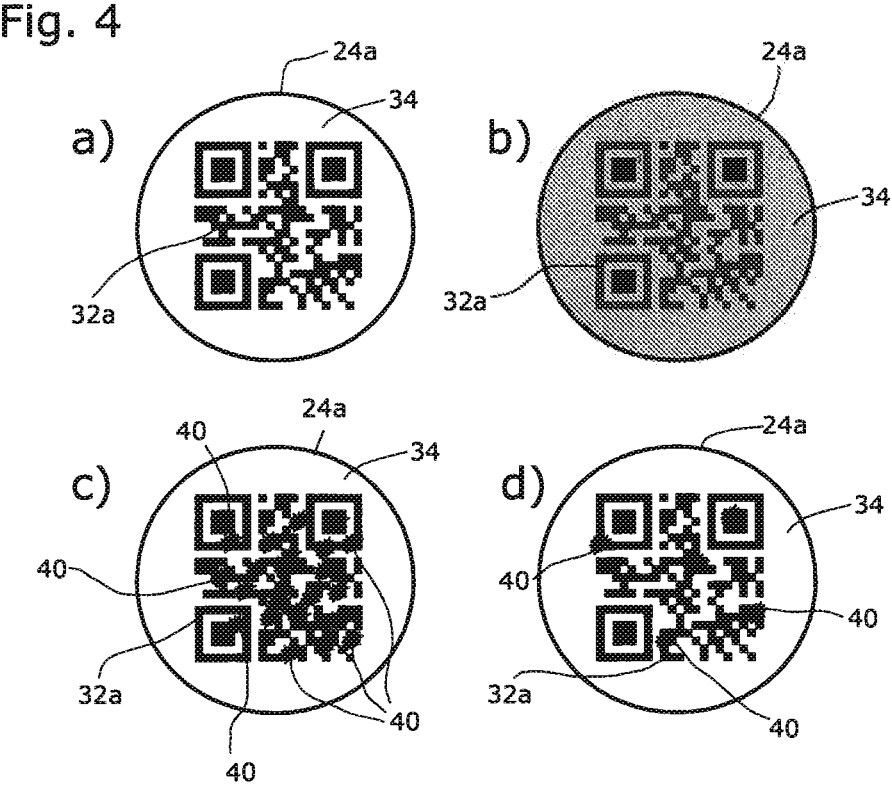
FIG. 4 shows, in sub-figures a) to d), different configurations when identifying the identification patterns in the sample liquid in a magnified illustration.

In sub-figures a) to d), FIG. 4 shows different situations as can be recorded by the camera 22. FIG. 4a shows a case with a clearly identifiable identification pattern 32a. Here, the sample liquid 34 situated between the image plane (camera 22 or the sensor 36 thereof) and the identification pattern 32a is transparent or clear.

FIG. 4b shows the case with a clear but darker colored sample liquid 34, which covers the identification pattern 32a. In such a case, the contrast between black (light opaque) and brighter (light transmissive) regions of the identification pattern 32a is less pronounced and may lead to difficulties when identifying the identification pattern 32a. Here, more bright conditions by means of the associated light source may possibly enable improved identification.

FIG. 4c schematically shows a multiplicity of undissolved particles 40, which are situated in the sample liquid in an undissolved state. The substance particles 40 cover relatively large regions of the identification pattern 32a, and so the latter can no longer be identified as such. Evaluation of the image data of such recordings of an identification pattern leads to the result that no identification pattern was identified.

FIG. 4d shows a case in which only a few undissolved substance particles are contained in the sample liquid. These cover the identification pattern 32a at a few points. Since an identification by means of an identification algorithm generally also comprises an error correction when identifying the identification pattern stored in the image data, an identification pattern only slightly falsified thus can nevertheless be identified as such, wherein however a value representing the error correction assumes a size which is significant for the presence of errors in the identification pattern.

Figure 5:
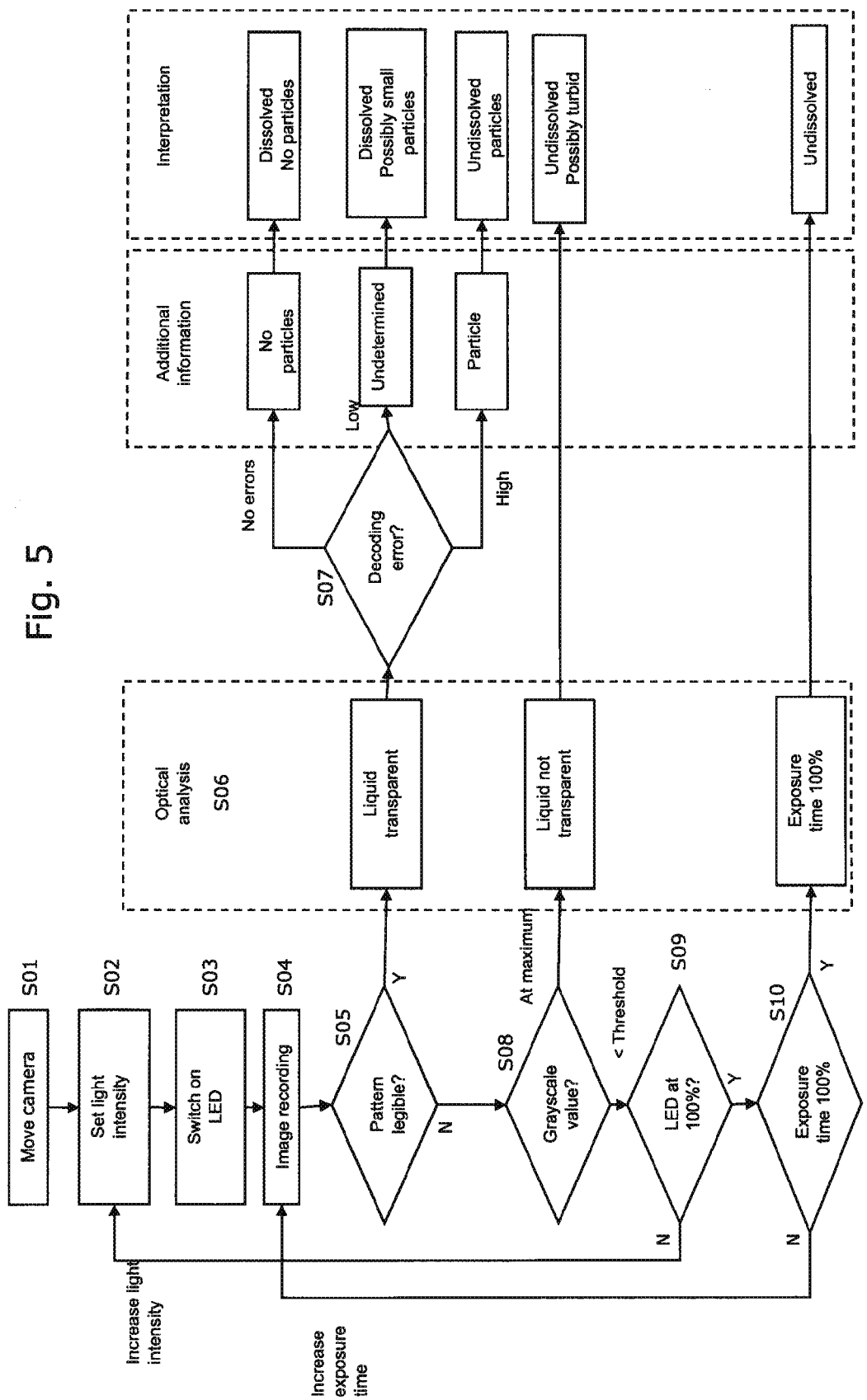
FIG. 5 shows a flowchart of an embodiment of the method according to the invention.

The method to be carried out by means of an analysis device or metering apparatus, as was described with reference to FIGS. 1-3, is illustrated clearly in FIG. 5. In a first step S01, the camera 22 or else several cameras is/are moved into a recording position above a specific sample container. In step S02, the light intensity of the associated light source, in particular a light-emitting diode 18a-h associated with the sample container, is set, the light-emitting diode is subsequently switched on in step S03 and an image is recorded in step S04 with the capture of corresponding image data of the identification pattern of the relevant sample container recorded through the sample liquid. An evaluation takes place in step S05, as to whether the identification pattern can be read. This step occurs within the scope of an identification algorithm. To the extent of that identification pattern being readable, an optical analysis S06 determines that the sample liquid is clear or transparent. A check is then carried out in step S07 whether there were errors when identifying the identification pattern, i.e. when decoding the information contained in the identification pattern, which errors were optionally taken into account or corrected by the error correction. If there are no errors, the assumption is made that the identification or decoding of the identification pattern took place without activating the error correction or that the value representing the error correction corresponds to a predetermined intended value, e.g. zero. From this, it is possible to obtain as additional information to the result of the optical analysis the information that no substance particles are present anymore and hence all particles have been dissolved in the sample liquid. This information can then be stored and processed further as interpretation or result of the optical analysis/identification of the identification pattern for the relative sample container.

If the error correction is small (low), an (undetermined) item of additional information, not determined in any more detail, is assumed. This allows the conclusion to be drawn or the interpretation to be made that either all particles have been dissolved or else that a few small particles are still present in the sample liquid in an undissolved state. In such a case, a threshold may optionally be implemented for the error correction, the dropping below or exceeding of which outputting a complete dissolution of the particles as a result or else indicating undissolved particles.

If the error correction is high, the assumption is made that it still has undissolved particles in the sample liquid; hence, it is still necessary to wait until these particles have also dissolved before the sample liquid is used further. By way of example, this can be re-checked after specific period of time by means of the optical analysis.

If it is determined in step S05 that the identification pattern cannot be read, a grayscale value which represents the transparency of the sample liquid is checked (S08). If this grayscale value reaches a maximum, the assumption is made that the sample liquid is not clear. From this, it is possible to conclude that very many undissolved substance particles are still present in the sample solution or else that the sample liquid has a very dark color which does not offer the required transparency for detecting the identification pattern. If the grayscale value lies below a certain threshold, a check is carried out in step S09 as to whether the brightness of the light-emitting diode is already 100%. If this is not the case, the brightness is increased and there is another analysis at step S02. If the light intensity is already 100% (S09), a check is carried out as to whether the exposure time of the camera has already been employed to 100% (S10). If this is the case, it is determined in S06 that the liquid sample is not transparent and the conclusion is drawn from this that the substance particles are not dissolved. If the exposure time is not yet 100%, a further image recording (S04) is carried out after increasing the exposure time and a new optical analysis is carried out.

As becomes apparent from the flowchart, parameters such as the light intensity (brightness) of the light source and the exposure time of the camera can be modified in the case of illegible or unidentified identification pattern and the optical analysis can be carried out again with the modified, in particular increased, parameters. This renders it possible for identification patterns initially not identified in a first analysis to be able, if required, to be identified without problems with modified parameters. Hence errors in the identification can be reduced or avoided.

Figure 6:
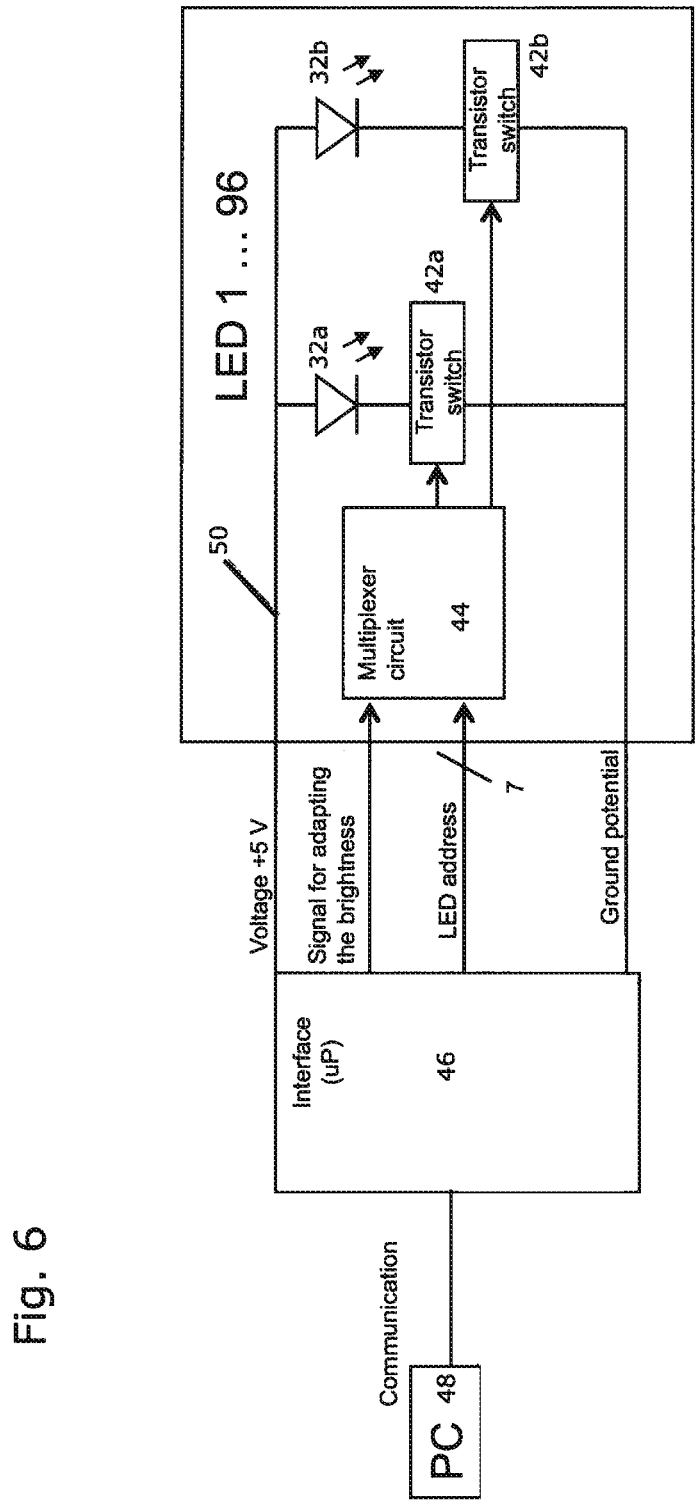
FIG. 6 shows an electrics diagram for actuating an embodiment of a light source for the method.

FIG. 6 finally shows, in a schematic illustration, the actuation of light-emitting diodes 32a, 32b of an array of preferably 96 light-emitting diodes. The light-emitting diodes 32a, 32b are switched by respective transistor switches 42a, 42b, which are connected to a multiplexer circuit 44. To this end, the multiplexer circuit 44 obtains from an interface 46 connected to a computer (PC) 48 a signal for adapting the brightness (light intensity) and information in respect of the address of the light-emitting diode, i.e. which light-emitting diode of the array should be made to shine with the desired brightness. The computer (PC) 48 is generally part of the metering apparatus, particularly automated pipetters. In the present example, the light-emitting diodes 32a, 32b are supplied with energy by a supply line 50 with a voltage of 5 V.

The optical analysis method presented here utilizes the presence of identification patterns on sample containers in order to be able to draw conclusions in respect of the transparency of the sample liquid held in the sample container by the degree of identifiability of the pattern. It therefore constitutes a simple and cost-effective type of quality assurance if the point is to determine whether a substance has dissolved in the sample liquid.

The invention claimed is:

1. A method for the optical analysis of a sample liquid (34) contained in a sample container (24a-h), wherein the sample liquid (34) contains at least one substance (40) in an at least partly dissolved form, comprising the steps of:
   providing at least one sample container (24a-h) filled with a sample liquid (34);
   illuminating the at least one sample container (24a-h) by means of a light source (18a-h); and
   capturing an image of an identification pattern (32a-h) associated with the at least one sample container (24a-h) by means of an image recording device (22) which generates image data, wherein the optical path (OP) is selected in such a way that the sample liquid (34) contained in the at least one sample container (24a-h) is at least partly situated between the image recording plane (36) of the image recording device (22) and the identification pattern (32a-h),
   wherein, after the image of the identification pattern (32a-h) has been recorded, the generated image data are evaluated and it is established whether the identification pattern (32a-h) can be identified (S05, S06) through the sample liquid (34),
   wherein, if the identification pattern (32a-h) of the at least one sample container (24a-h) is identified, it is established how large the error correction is and derived therefrom whether the substance (40) is partly or completely dissolved in the sample liquid (34).

2. The method as claimed in claim 1, wherein a light source (18a-h) is associated with the at least one sample container (24a-h).

3. The method as claimed in claim 1, wherein the light source (18a-h) or each light source is set in terms of its brightness.

4. The method as claimed in claim 1, wherein, after identifying the identification pattern (32a-h), it is established whether the identification pattern (32a-h) was identified (S07) with or without error correction.

5. The method as claimed in claim 1, wherein, if the identification pattern (32a-h) of the at least one sample container (24a-h) is not identified, the presence of an undissolved substance (40) in the sample liquid (34) is assumed as a result; in particular, the sample liquid (34) is assumed to be turbid.

6. The method as claimed in claim 2, wherein the brightness of the light source (18a-h) is set (S09) depending on the identification of the identification pattern (32a-h).

7. The method as claimed in claim 2, wherein the exposure duration of the image recording device is set (S10) depending on the identification of the identification pattern (32a-h).

8. The method as claimed in claim 2, wherein the method steps (S02-S10) are at least in part carried out several times for the at least one sample container (24a-h), wherein, preferably, in the case of each renewed run-through, the brightness of the light source (18a-h; S09) and/or the exposure duration of the image recording device (22; S10) is modified.

9. An analysis device for carrying out the method as claimed in claim 1, wherein the analysis device comprises:
   at least one light source (18a-h) for illuminating at least one sample container (24a-h) held in a holding container, wherein the holding container and the light source (18a-h) can preferably be moved relative to one another and wherein an identification pattern (32a-h) is arranged on the sample container (24a-h),
   at least one image recording device for capturing the identification pattern (32a-h) of the at least one sample container (24a-h), wherein the image recording device and the holding container are arranged in such a way that they can move relative to one another,
   wherein, in relation to the optical path (OP), the image recording device is provided on the analysis device in such a way that the sample liquid (34) contained in the at least one sample container (24a-h) is at least partly situated between the image recording plane (36) of the image recording device (22) and the identification pattern (32a-h), wherein it furthermore comprises a control device, which is configured in such a way that the method steps required for the optical analysis of the sample liquid (34) can be carried out.

10. The analysis device as claimed in claim 9, wherein light originating from the light source (18*a-h*) is guided in such a way that it irradiates the at least one sample container (24*a-h*) on the underside thereof.

11. The analysis device as claimed in claim 10, wherein the light source (18*a-h*) is arranged below the holding container or the at least one sample container (24*a-h*) situated therein and wherein, preferably, the image recording device is arranged above the sample container (24*a-h*) irradiated by the light source (18*a-h*).

12. The analysis device as claimed in claim 9, wherein the holding device is embodied in such a way that a plurality of sample containers (24*a-h*) can be held therein in the style of a matrix with n columns and m rows.

13. The analysis device as claimed in claim 12, wherein the light source is formed by a plurality of light-emitting diodes (18*a-h*), which are preferably arranged, in a manner corresponding to the matrix arrangement of the holding container, in such a way that a light-emitting diode (18*a-h*) can be associated with each sample container of the holding container.

14. The analysis device as claimed in claim 9, wherein the identification pattern (32*a-h*) on the at least one sample container (24*a-h*) is provided on the underside thereof, wherein the identification pattern (32*a-h*) is preferably formed by various regions with different light transmission properties.

15. The analysis device as claimed in claim 9, wherein the control device is further configured in such a way that the actuation of the relative movements between holding container, light source (18*a-h*) and image recording device can be carried out.

16. The analysis device as claimed in claim 9, wherein it is part of a metering apparatus, in particular an automated pipetter.

\* \* \* \* \*